United States Patent [19]

Zurflüh

[11] Patent Number: 4,625,048

[45] Date of Patent: Nov. 25, 1986

[54] CARBAMIC ACID ESTERS

[75] Inventor: René Zurflüh, Bülach, Switzerland

[73] Assignee: Hoffmann-La Roche Inc., Nutley, N.J.

[21] Appl. No.: 684,412

[22] Filed: Dec. 20, 1984

Related U.S. Application Data

[63] Continuation of Ser. No. 408,089, Aug. 13, 1982, abandoned.

[51] Int. Cl.$^4$ ............................................. C07C 125/06
[52] U.S. Cl. ........................................ 560/166; 564/74
[58] Field of Search ........................... 560/166; 564/74; 514/478, 489

[56] References Cited

U.S. PATENT DOCUMENTS 4,060,629 11/1977 Karrer .................................. 560/166
4,080,470 3/1978 Karrer .................................. 560/166

FOREIGN PATENT DOCUMENTS 1577181 10/1980 United Kingdom ................ 560/166

*Primary Examiner*—Paul J. Killos
*Attorney, Agent, or Firm*—Jon S. Saxe; George M. Gould; Patricia A. Coburn

[57] ABSTRACT

Carbamic acid esters of the formula

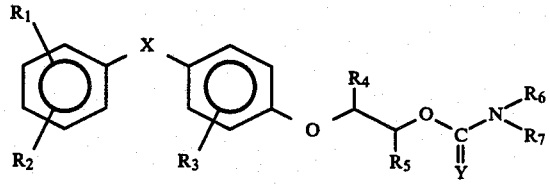

wherein $R_1$, $R_2$, $R_3$, $R_4$, $R_5$, $R_6$, $R_7$, X, and Y are as defined hereinafter, process for their preparation, as well as pesticidal compositions containing these compounds as the active ingredient and methods for using the pesticidal compositions for the control of pests are described.

14 Claims, No Drawings

CARBAMIC ACID ESTERS

SUMMARY OF THE INVENTION

This is a continuation of application Ser. No. 408,089 filed 8/13/82, abandoned.

The invention is concerned with carbamic acid esters of the formula

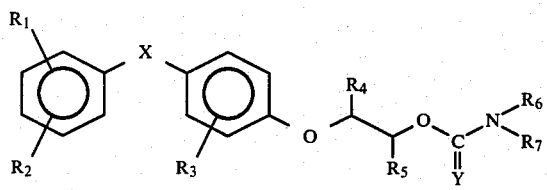

wherein $R_1$ is hydrogen, halogen, or methyl, $R_2$ is halogen, methyl, or trifluoromethyl, $R_3$ is hydrogen, halogen, or methyl, $R_4$ and $R_5$ are hydrogen or methyl, $R_6$ is hydrogen, methyl, or ethyl, $R_7$ is methyl, ethyl, or isopropyl, X is oxygen, sulfur, methylene, or carbonyl, and X is oxygen or sulfur, whereby, when X is sulfur, methyl, or carbonyl, or $R_3$ is halogen or methyl, $R_2$ can also be hydrogen.

In another aspect, the invention relates to pesticidal compositions and methods of use.

DETAILED DESCRIPTION OF THE INVENTION

The present invention comprises carbamic acid esters of the formula

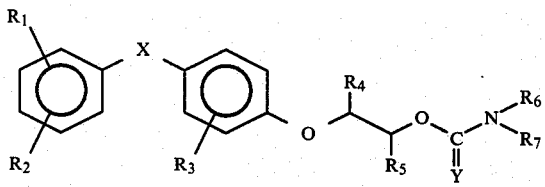

wherein $R_1$ is hydrogen, halogen, or methyl, $R_2$ is halogen, methyl, or trifluoromethyl, $R_3$ is hydrogen, halogen, or methyl, $R_4$ and $R^5$ are hydrogen or methyl, $R_6$ is hydrogen, methyl, or ethyl, $R_7$ is methyl, ethyl, or isopropyl, X is oxygen, sulfur, methylene, or carbonyl, and Y is oxygen or sulfur, whereby, when X is sulfur, methylene, or carbonyl or $R_3$ is halogen or methyl, $R_2$ can also be hydrogen.

As used herein, the term "halogen" denotes fluorine, chlorine, bromine, or iodine. The symbols $R_4$ and $R_5$ can have the same or different meanings, but $R_4$ and $R^5$ preferably do not simultaneously denote methyl.

Since the compounds of formula I can contain asymmetric carbon atoms, they can exist as optical antipodes. Formula I is, accordingly, intended to include all of these possible isomeric forms.

If $R_1$ or $R_2$ denotes halogen, then this is preferably fluorine, chlorine, or bromine. If $R_3$ denotes halogen, this is preferably fluorine or chlorine.

An interesting sub-group of compounds of formula I comprises those compounds in which $R_2$ denotes halogen, methyl, or trifluoromethyl and, when X denotes sulfur, methylene or carbonyl, $R_2$ can also be hydrogen.

Independently of one another $R_1$ preferably denotes hydrogen, m-halogen or m-methyl, $R_2$ preferably denotes hydrogen, p-fluoro, m-chloro, m-bromo, m-methyl or m-trifluoromethyl and $R_3$ preferably denotes hydrogen or fluorine.

$R_4$, $R_5$, and $R_6$ each preferably denote hydrogen.
X preferably denotes oxygen.
Preferred compounds of formula I are:
[2-[p-(m-Fluorophenoxy)phenoxy]-ethyl]N-ethylcarbamate,
[2-[p-(p-fluorophenoxy)phenoxy]-ethyl]N-ethylcarbamate,
[2-(o-fluoro-p-phenoxy-phenoxy)-ethyl]N-ethylcarbamate and
[2-[p-(m-chlorophenoxy)phenoxy]-ethyl]N-ethylcarbamate.

Representative compounds of formula I are:
[2-[p-(p-Fluorophenoxy)phenoxy]-ethyl]N-methylcarbamate,
[2-[p-(m-bromophenoxy)phenoxy]-ethyl]N-ethylthiocarbamate,
[2-[p-(p-fluorophenoxy)phenoxy]-ethyl]N-ethylthiocarbamate,
[2-[p-(α,α,α-trifluoro-m-tolyloxy)phenoxy]-ethyl N-ethylcarbamate,
[2-[p-(m-chlorophenoxy)phenoxy]-ethyl]N-ethylthiocarbamate,
[2-[p-(m-fluorophenoxy)phenoxy]-ethyl]N-ethylthiocarbamate and
[2-(m-fluoro-p-phenoxy-phenoxy)-ethyl]N-ethylcarbamate.

The compounds of formula I are prepared by one of the procedures described below.

(A) Compounds of formula I wherein $R_6$ denotes hydrogen can be prepared by reacting an alcohol of the general formula

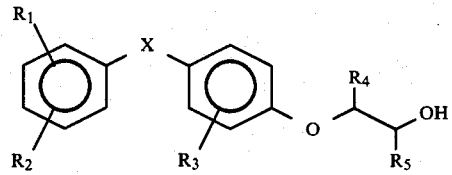

wherein $R_1$, $R_2$, $R_3$, $R_4$, $R_5$, and X are as described previously,
with an isocyanate or isothiocyanate of the general formula $$R_7-N=C=Y \qquad III$$

wherein $R_7$ and Y are as described previously.

The reaction is conveniently carried out in the presence of an inert diluent, especially an organic solvent, as well as preferably in the presence of a catalyst.

Examples of inert organic solvents which can be used in this process include ethers and ether-like compounds, such as diethyl ether, 1,2-dimethoxyethane, tert.butyl methyl ether, dioxan and tetrahydrofuran; hydrocarbons, for example, n-hexane and toluene; halogenated hydrocarbons, for example, methylene chloride, chloroform, carbon tetrachloride, and the like; ketones, for example, acetone, 2-butanone and 3-pentanone; nitriles, for example, acetonitrile and propionitrile; formamides, for example, dimethylformamide; and pyridine.

Preferred catalysts for this reaction are tertiary bases, such as triethylamine and 1,4-diazabicyclo(2,2,2)octane; and tin-organic compounds such as dibutyl-tin diacetate.

The reaction temperature can be varied over a wide range, but generally the reaction is carried out at a temperature between 0° C. and the reflux temperature of the reaction mixture, preferably between room temperature and the reflux temperature. When the reaction is run at the preferred temperature range, the reaction is normally completed within a day.

In carrying out this reaction an excess of isocyanate or isothiocyanate of formula III is preferably used. In order to isolate the resulting compound of formula I, excess isocyanate or isothiocyanate and diluent which may be present can be removed, for example by distillation, and the residue can be purified using conventional methods, for example, by column chromatography and/or crystallization.

(B) Compounds of formula I wherein $R_6$ is methyl or ethyl can be prepared by reacting an alcohol of general formula II, as described previously, with a carbamic acid halide or thiocarbamic acid halide of the general formula

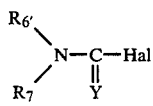

IV wherein $R_{6'}$ is methyl or ethyl, Hal is halogen, preferably chlorine, and $R_7$ and Y are as described previously.

This reaction is conveniently carried out in the presence of an inert diluent, especially an organic solvent, as well as in the presence of an acid-binding agent.

Preferred organic solvents are the solvents referred to about in connection with process A above.

Examples of acid-binding agents which can be used in this reaction are conventional inorganic and organic acid-binding agents, preferably alkali carbonates, such as sodium carbonate, potassium carbonate, and sodium bicarbonate; lower tertiary alkylamines, cycloalkylamines and arylalkylamines, especially triethylamine; pyridine; and 1,4-diazabicyclo(2,2,2)octane.

The reaction temperatures can be varied over a wide range in carrying out this process variant; however, the reaction is generally carried out at a temperature between 0° C. and the boiling point of the reaction mixture.

1 to 2 mole of carbamic acid halide or thiocarbamic acid halide of formula IV is preferably used for each mole of the alcohol of formula II. In addition, it has been found to be advantageous to use the acid-binding agent in slight excess, for example, up to about 30 weight percent. The isolation of the resulting compound of formula I can be carried out using conventional techniques.

(C) Reacting an alcohol of general formula II, as previously described, with phosgene or thiophosgene and subsequently an amine of the general formula

V wherein $R_6$ and $R_7$ are as described above.

The reaction is conventiently carried out in the presence of an inert diluent, especially an organic solvent, as well as in the presence of an acid-binding agent.

Especially preferred organic solvents are ethers and ether-like compounds, such as 1,2-dimethoxyethane, dioxan, and tetrahydrofuran; nitriles, for example acetonitrile; formamides, for example, dimethylformamide; and hydrocarbons, for example toluene. All usually usable inorganic and organic acid-binding agents, to which preferably belong the acid-binding agents mentioned above in connection with the procedure B above, can be added.

The reaction temperatures can be varied in a wide range in carrying out this reaction. In general, the reaction is carried out at temperatures between about 0° C. and 100° C., preferably between 0° C. and 40° C.

The process is conveniently carried out as a one-pot process. Phosgene or thiophosgene is reacted with the alcohol of formula II and then the amine of formula V is added to the reaction mixture. It has been found to be advantageous to use 1 to 1.5 mole of phosgene or thiophosgene and 1 to 1.5 mole of the amine of formula V for each mole of the alcohol of formula II. Further, the acid-binding agent is preferably used in slight excess, for example, up to about 30 weight percent. The isolation of the thus-obtained compound of formula I can be carried out in the usual manner.

Insofar as no planned synthesis for the isolation of pure isomers is carried out, a product is normally obtained as a mixture of two or more isomers. The isomers can be separated according to known methods.

The compounds of formulae II-V which are used as starting materials are either known or can be prepared according to known methods.

The alcohols of formula II in which either $R_4$ is hydrogen and $R_5$ is hydrogen or methyl or $R_4$ and $R_5$ both are methyl can be prepared, for example, by the addition of a corresponding 1,2-epoxide of the formula

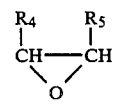

VI wherein either $R_4$ is hydrogen and $R_5$ is hydrogen or methyl, or $R_4$ and $R_5$ both are methyl, to a phenol of the formula.

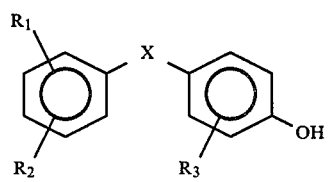

VII wherein $R_1$, $R_2$, $R_3$, and X are as previously described.

One embodiment of this reaction is described, for example, in Houben-Weyl, Methoden der Organischen Chemie, Volume VI/3, from page 79. For the preparation of the alcohols of formula II in which $R_4$ and $R_5$ both are hydrogen, the phenol of formula VII can be reacted with ethylene carbonate. One embodiment of this reaction is described in Houben-Weyl, Methoden der Organischen Chemie, Volume VI/3, p. 75.

The alcohols of formula II in which $R_4$ is methyl and $R_5$ is hydrogen can be prepared, for example, by reducing an ester of the formula

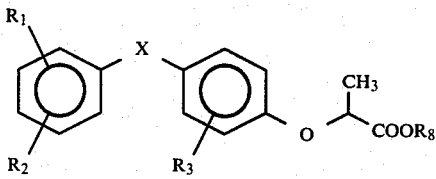

VIII wherein $R_1$, $R_2$, $R_3$, and X are as previously described and $R_8$ is lower alkyl, preferably $C_{1-4}$-alkyl, conveniently using a complex metal hydride, for example, lithium aluminium hydride, in an inert organic solvent, preferably diethyl ether or tetrahydrofuran, and in a temperature range between $-10°$ C. and the boiling point of the reaction mixture. The isolation of the resulting alcohol of formula II can be carried out using conventional procedures.

The isocyanates or isothiocyanates of formula III can be prepared, for example, by reacting the respective amine $R_7NH_2$ with phosgene or thiophosgene and subsequently heating.

For the preparation of the carbamic acid chlorides or thiocarbamic acid chlorides of formula IV, the respective amine $R_6·R_7NH$ can, for example, be reacted with phosgene or thiophosgene.

The compounds of formula I of this invention are active as pesticides and especially useful for the control of insects, Acarina, especially ticks, and nematodes. They are especially valuable against:

Lepidoptera such as, for example, Adosophyes spp, Tortrix viridana, Cheimatobia brumata, Lyonetia clerkella, Operophtera brumata, Lithocolletis blancardella, and other boring moths, Laspeyresia spp., Porthetria dispar, Orgyis spp., Choristoneura spp., Clysia ambiguella, Lobesia bortana, Agrotis segetum, Heliothis spp., Spodoptera spp., Ostrinia nubilalis, Ephestia spp., Galleria mellonella, Plodia interpunctella, Pectinophora gossypiella;

Homoptera, i.e., Shield and soft lice such as, for example, Aspidiotus spp., Saissetia spp., Quadraspidiotus perniciosus, Aonidiella aurantii, Coccus spp., Unaspis spp., Lecania spp., as well as Lepidosaphes spp., Planococcus spp., Pseudococcus spp., Ceroplastes spp., Icerya purchasi, Chrysomphalus spp., Parlatoria spp., Rhizoecus spp., as well as cicada such as, for example, Nephotettix spp., Laodelphax spp., Nilaparvata spp., as well as leaf suckers such as, for example Psylla mali, Psylla piri, psylla pirisuga, Psylla piricula, trioza apicalis, as well as aphids such as, for example, Aphis fabae, Myzus persicae, as well as white flies such as, for example, Trialeurodes vaporariorum, Aleurodes proletella, Bemisia tabaci;

Diptera such as, for example, Aedes aegypti, Culex pipiens, Aedes taeniorrhynchus, Anopheles stephensi, Calliphora spp., Musca domestica, Sciara spp., Phorbia spp., Sciaridae and Thoridae spp.;

Coleoptera such as, for example, Oryzaephilus surinamensis, Rhizopertha dominica, Sitophilus granarius, Sitophilus oryzae, Tenebrio molitor, Tribolium castaneum, Trogoderma granarium, Lasioderma serricorne, Epilachna spp., Leptinotarsa spp., Otiorhynchus sulcatus, Diabrotica spp. and other soil Coleoptera;

Orthoptera such as, for example, Blattella germanica, Leucophaea surinamensis, Nauphoeta cinerea, Blatta orientalis, Periplaneta americana;

Heteroptera such as, for example, Dysdercus cingulatus, Rhodnius prolixus, Oncopeltus fasciatus, Lygus spp., Piesma spp.;

Isoptera (termite species);

Siphonaptera (fleas);

Hymenoptera such as, for example, Solenopsis invicta, Monomorium pharaonis, Atta spp. as well as true sawflies such as, for example, Athalia rosae, Hoplocampa spp., Pristiphora spp.;

Acarina such as, for example, Tetranychus urticae, Tetranychus cinnabarinus, Panonychus ulmi and other Tetranychida, Eriophyida such as Phyllocoptruta oleivora, furthermore ticks such as, for example, Amblyomma spp., Boophilus spp. and other Ixodoida;

Nematoda such as, for example, Ditylenchus dipsaci, Meliodogyne incognita, Pratylenchus penetrans, Aphelenchoides rizemabosi and Globodera rostochiensis.

The carbamic acid ester compounds of this invention are active as pesticides wherein they function both as contact and feed poisons. They also possess pesticidal activity in the vapor phase. In contrast to most of the known pesticides, which act as toxins on the nervous system of the animals and thereby kill, cripple or repel them, the compounds of formula I interfere with the specific hormonal system of the insects. Thereby, for example, the metamorphosis to the imago, the laying of viable eggs, and the development of laid normal eggs is disturbed. Moreover, in some insect species the larval moultings are disturbed. The sequence of generations is interrupted, and the insects are indirectly killed. The compounds are also active on the most varied pests which have resistance to known pesticides. However, they are harmless to various useful arthropods.

In addition to pesticidal properties, the compounds of formula I also have particular properties which produce an improvement in the quality and/or quantity of the silk thread in sericulture. They can, therefore, be used in sericulture. To this end, the compounds of formula I can be used, for example, as additives to the feed of silkworms.

For practical purposes, the compounds of formula I can be said to be substantially non-toxic to vertebrates. The toxicity of the compound of formula I is on average above 1000 mg per kg of body weight. The compounds of formula I are also readily degraded, and the danger of a cumulation is, therefore, excluded. Accordingly, the carbamic acid ester compounds of this invention are useful for the control of pests on animals, plants, provisions, and materials, as well as in water.

The invention is also directed to pesticidal compositions which comprise inert carrier material and, as the active ingredient, a compound of formula I. These compositions conveniently contain, as the inert carrier material, at least one of the following ingredients: solid carrier materials; solvents or dispersion media; surface active agents, for example, wetting and emulsifying agents; dispersing agents; and stabilizers.

Examples of solid carrier materials include natural mineral substances, such as kaolin, aluminas, siliceous earth, talc, bentonite, chalk, limestone, quartz, dolomite, attapulgite, montmorillonite and diatomaceous earth; synthetic mineral substances, such as highly dispersible silicic acid, aluminium oxide and silicates; organic substances, such as cellulose, starch, urea and synthetic resins; and fertilizers, such as phosphates and nitrates, whereby such carrier substances can be present, for example, as dusts, powders, or granulates.

Examples of liquid solvents or dispersion media include: aromatics, such as toluene, xylenes and alkylnaphthalenes, chlorinated aromatics and chlorinated aliphatic hydrocarbons, such as chlorbenzenes, chloroethylenes and methylene chloride; aliphatic hydrocarbons, such as cyclohexane and paraffins (e.g., petroleum fractions); alcohols, such as butanol and glycol, as well as their ethers and esters; ketones, such as acetone, methyl ethyl ketone, methyl isobutyl ketone and cyclohexanone; and strongly polar solvents, such as dimethylformamide, N-methylpyrrolidone and dimethylsulfoxide, whereby such solvents or dispersion media preferably have flash points of at least 30° C. and boiling points of at least 50° C., and water. When water is used as the solvent, organic solvents can also be used as auxiliary solvents.

Included among the solvents are dispersion media are the so-called liquified gaseous extenders or carrier substances. By liquified gaseous extenders or carrier substances are meant liquids which are gaseous at normal temperature and under normal pressure, such as aerosol propellants, e.g., halogenated hydrocarbons (e.g., dichlorodifluoromethane).

Surface active agents, especially emulsifying agents and wetting agents, suitable for use in the pesticidal compositions of this invention can be non-ionic, anionic, or cation compounds.

Examples of non-ionic compounds which can be used include condensation products of fatty acids, fatty alcohols, or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

Examples of anionic compounds include soaps; fatty sulfate esters, such as dodecyl sodium sulfate, octadecyl sodium sulfate, and cetyl sodium sulfate; alkyl sulfonates, aryl sulfonates, and fatty-aromatic sulfonates, such as alkylbenzene sulfonates, for example, calcium dodecylbenzene sulfonate and butylnaphthalene sulfonates; and more complex fatty sulfonates, for example, the amide condensation products of oleic acid and N-methyltaurine and the sodium sulfonate of dioctyl succinate.

Examples of cationic compounds include alkyldimethylbenzylammonium chlorides, dialkyldimethylammonium chlorides, alkyltrimethylammonium chlorides and ethoxylated quaternary ammonium chlorides.

Dispersing agents suitable for use in the pesticidal compositions of this invention are lignin, sodium and ammonium salts of lignin sulfonic acid, sodium salts of maleic acid anhydride-diisobutylene copolymers, sodium and ammonium salts of sulfonated polycondensation products of naphthalene and formaldehyde, and sulfite lyes. Dispersing agents, which are especially suitable as thickening or anti-settling agents, include methylcellulose, carboxymethylcellulose, hydroxyethylcellulose, polyvinyl alcohol, alginates, caseinates and blood albumin.

Stabilizers suitable for use in the pesticidal compositions of the present invention include acid-binding agents, such as epichlorohydrin, phenyl glycidyl ether and soya epoxides; antioxidants, such as gallic acid esters and butylhydroxytoluene; UV-absorbers, such as substituted benzophenones, diphenylacrylonitrile acid esters and cinnamic acid esters; and deactivators, such as salts of ethylenediaminotetraacetic acid and polyglycols.

The pesticidal compositions of this invention can contain, in addition to the active substances of formula I, other active substances, such as other pest control agents, pest baits, fungicides, batericides, herbicides, plant growth regulators and fertilizers. Such combination compositions are suitable for increasing the activity or for broadening the spectrum of activity. If necessary, inadequacies of known compositions can thereby also be balanced and improved.

The pesticidal compositions of the present invention can be prepared by known methods, for example, by mixing the active ingredient with solid carrier materials, by dissolution or suspension in suitable solvents or dispersion media, and, if necessary, using surface active agents, as wetting or emulsifying agents, or dispersing agents, or by diluting pre-prepared emulsifiable concentrates with solvents or dispersion media.

In preparing the pesticidal compositions of the present invention, the active ingredient of formula I is mixed with inert carrier material. In the case of pulverous composition, the active ingredient can be mixed with the solid carrier material, for example, by milling together, or the solid carrier material can be impregnated with a solution or suspension of the active ingredient and then the solvent or suspension medium can be removed by evaporation, heating or removing under reduced pressure. By the addition of wetting and/or dispersing agents, such pulverous compositions can be made readily wettable with water so that they can be converted into aqueous suspensions which are suitable, for example, as spray compositions.

The compounds of formula I can be mixed with a surface active agent and a solid carrier material to form a wettable powder which is dispersible in water, or they can be mixed with a solid pre-granulated carrier material to form a granulate.

For preparation of emulsifiable concentrates which are especially suitable for storage and shipment, the active ingredient can be dissolved in a water-immiscible solvent, such as, for example, an alicyclic ketone, which conveniently contains a dissolved emulsifying agent, so that the solution becomes self-emulsifying upon addition to water. Alternatively, the active ingredient can be mixed with an emulsifying agent, and the mixture can then be diluted with water to the desired concentration. Moreover, the active substance can be dissolved in a solvent, and thereafter the solution can be mixed with an emulsifying agent. Such a mixture can likewise be diluted with water to the desired concentration. In this manner there are obtained emulsifiable concentrates or ready-for-use emulsions.

The pesticidal compositions of this invention generally contain between 0.0005 percent by weight and 95 percent by weight of compound or compounds of formula I as active ingredient, preferably between 0.5 percent by weight and 90 percent by weight.

The pesticidal compositions of the present invention can be in forms suitable for storage or shipment. In such forms (e.g., emulsifiable concentrates), the concentration of active ingredients is normally at the higher end of the above concentration range. These forms can then be diluted with the same or different carrier materials to afford active ingredient concentrations suitable for practical use, and such concentrations normally lie at the lower end of the above-noted concentration range. Emulsifiable concentrates generally contain from about 5 percent by weight to about 95 percent by weight of the compound or compounds of formula I, preferably from about 10 percent by weight to about 90 percent by weight.

The application forms prepared from the above-indicated compositions include ready-for-use solutions, emulsions, foams, suspensions, powders, pastes, soluble powders, dusting agents and granulates.

The concentrations of active ingredient in the ready-for-use preparations can vary over wide limits. In spray liquors, the concentration can be, for example, between 0.0005 percent by weight and 20 percent by weight.

The active ingredients can also be used with good effect in the ultra-low-volume process (ULV) where it is possible to formulate spray liquors having preferably from about 0.5 to about 20 percent by weight of active ingredient.

The active ingredients can also be used with good effect in the low-volume process and in the high-volume process where it is possible to formulate spray liquors having from 0.02 to 1.0 and 0.002 to 0.1 percent by weight of active ingredient respectively.

In granulates which are especially useful in mosquito control, the concentration of active ingredient is preferably from about 1 to about 10 percent by weight of the compound or compounds of formula I as the active ingredient.

The present invention is also concerned with a method for the treatment of the locus to be protected or the pests themselves with a compound of this invention or with the pesticidal compositions of the present invention. This method of use is preferably carried out by applying the composition to the soil or leaves, or by application to animals, provisions, or materials to be protected, depending on the pests to be controlled. The control is achieved e.g. by contact or by intake with feed.

The pesticidal compositions can be applied in a conventional manner, such as by sprinkling, spraying, smoke-screening, dusting, scattering, drilling-in, vaporizing, pouring, soaking or incrustating. Pulverous preparations can be applied to the pests or to the objects to be protected, such as plants or animals, as, for example, dusting agents using the usual dusting apparatuses. Aqueous suspensions can be used, for example, as spray compositions.

The following examples illustrate the invention.

PREPARATION OF THE ACTIVE SUBSTANCES OF FORMULA I

Example 1

1 drop of dibutyl-tin diacetate and 0.6 g of ethyl isocyanate are added to a solution of 1.9 g of 2-[p-(p-fluorophenoxy)phenoxy]-ethanol in 20 ml of toluene. The mixture is subsequently stirred at 40° C. for 2 hours.

For the working-up, the mixture is firstly washed with 50 ml of water, and the aqueous phase is extracted with 50 ml of diethyl ether. The combined organic phases are subsequently dried with anhydrous sodium sulfate and evaporated. The residue, which is initially oily and then solidifies, is recrystallized from diisopropyl ether to yield pure [2-[p-(p-fluorophenoxy)phenoxy]-ethyl]N-ethylcarbamate; m.p. 60°-62° C.

In an analogous manner:

from 2-[p-(p-fluorophenoxy)phenoxy]-ethanol and isopropyl isocyanate there is obtained [2-[p-(p-fluorophenoxy)phenoxy]-ethyl]N-isopropylcarbamate, m.p. 78°-79° C.;

from 2-[p-(p-fluorophenoxy)phenoxy]-ethanol and methyl isocyanate there is obtained [2-[p-(p-fluorophenoxy)phenoxy]-ethyl]N-methylcarbamate, m.p. 85°-87° C.;

from 2-[p-(p-fluorophenoxy)phenoxy]-propanol and ethyl isocyanate there is obtained [2-[p-(p-fluorophenoxy)phenoxy]-propyl]N-ethylcarbamate, $n_D^{20}=1.5330$;

from 2-[p-(α,α,α-trifluoro-m-tolyloxy)phenoxy]-ethanol and ethyl isocyanate there is obtained [2-[p-(α,α,α-trifluoro-m-tolyloxy)phenoxy]-ethyl]N-ethylcarbamate, m.p. 66°-68° C.;

from 2-[p-(m-fluorophenoxy)phenoxy]-ethanol and ethyl isocyanate there is obtained [2-[p-(m-fluorophenoxy)phenoxy]-ethyl]N-ethylcarbamate, m.p. 58°-60° C.;

from 1-[p-(m-fluorophenoxy)phenoxy]-2-propanol and methyl isocyanate there is obtained [2-[p-(m-fluorophenoxy)phenoxy]-1-methyl-ethyl]N-methylcarbamate, $n_D^{20}=1.5450$;

from 1-[p-(m-fluorophenoxy)phenoxy]-2-propanol and ethyl isocyanate there is obtained [2-[p-(m-fluorophenoxy)phenoxy]-1-methyl-ethyl]N-ethylcarbamate, $n_D^{20}=1.5392$;

from 2-(p-benzoylphenoxy)-ethanol and ethyl isocyanate there is obtained [2-(p-benzoylphenoxy)-ethyl]N-ethylcarbamate, m.p. 87°-90° C.;

from 2-(p-benzylphenoxy)-ethanol and ethyl isocyanate there is obtained [2-(p-benzylphenoxy)-ethyl]N-ethylcarbamate, m.p. 76°-77° C.;

from 2-[p-(m-chlorophenoxy)phenoxy]-ethanol and ethyl isocyanate there is obtained [2-[p-(m-chlorophenoxy)phenoxy]-ethyl]N-ethylcarbamate, m.p. 76°-78° C.;

from 2-[p-(3,5-dichlorophenoxy)phenoxy]-ethanol and ethyl isocyanate there is obtained [2-[p-(3,5-dichlorophenoxy)phenoxy]-ethyl]N-ethylcarbamate, m.p. 82°-84° C.;

from 2-[p-(m-tolyloxy)phenoxy]-ethanol and ethyl isocyanate there is obtained [2-[p-(m-tolyloxy)phenoxy]-ethyl]N-ethylcarbamate, m.p. 46°-48° C.;

from 2-[p-(3-chloro-5-fluorophenoxy)phenoxy]-ethanol and ethyl isocyanate there is obtained [2-[p-(3-chloro-5-fluorophenoxy)phenoxy]-ethyl]N-ethylcarbamate, m.p. 80°-81° C.;

from 2-[p-(m-chloro-p-fluorophenoxy)phenoxy]-ethanol and ethyl isocyanate there is obtained [2-[p-(m-chloro-p-fluorophenoxy)phenoxy]-ethyl]N-ethylcarbamate, m.p. 70°-71.5° C.;

from 2-[o-fluoro-p-phenoxy-phenoxy]-ethanol and ethyl isocyanate there is obtained [2-(o-fluoro-p-phenoxy-phenoxy)-ethyl]N-ethylcarbamate, $n_D^{20}=1.5472$;

from 2-[m-fluoro-p-phenoxy-phenoxy]-ethanol and ethyl isocyanate there is obtained [2-(m-fluoro-p-phenoxy-phenoxy)-ethyl]N-ethylcarbamate, m.p. 56°-57° C.;

from 2-(p-phenylmercapto-phenoxy)-ethanol and ethyl isocyanate there is obtained [2-(p-phenylmercapto-phenoxy)-ethyl]N-ethylcarbamate, m.p. 63°-64° C.;

from 2-[p-(p-chlorophenylmercapto)phenoxy]-ethanol and ethyl isocyanate there is obtained [2-[p-(p-chlorophenylmercapto)phenoxy]-ethyl]N-ethylcarbamate, m.p. 92°-94° C.;

from 2-(p-phenoxy-m-tolyloxy)-ethanol and ethyl isocyanate there is obtained [2-(p-phenoxy-m-tolyloxy)-ethyl]N-ethylcarbamate, m.p. 52°–54° C.; and from 2-[p-(3,5-xylyloxy)phenoxy]-ethanol and ethyl isocyanate there is obtained [2-[p-(3,5-xylyloxy)-phenoxy]-ethyl]N-ethylcarbamate, m.p. 67°–68° C.

EXAMPLE 2

50 mg of 1,4-diazabicyclo(2,2,2)octane and 0.9 g of ethyl isothiocyanate are added to a solution of 2.3 g of 2-[p-(p-fluorophenoxy)phenoxy]-ethanol in 10 ml of pyridine. The mixture is then allowed to stir at 80° C. for 16 hours. The cooled mixture is poured into 50 ml of ice/water and extracted three times with 80 ml of ethyl acetate each time. The extracts are washed twice with 50 ml of water each time and with 50 ml of sodium chloride solution. The extracts are dried over anhydrous sodium sulfate and evaporated. The residue is purified chromatography on silica gel with n-hexane/ethyl acetate (2:1) to yield pure [2-[p-(p-fluorophenoxy)phenoxy]-ethyl]N-ethylthiocarbamate; m.p. 73°–75° C.

In an analogous manner:

from 2-[p-(m-bromophenoxy)phenoxy]-ethanol and ethyl isothiocyanate there is obtained [2-[p-(m-bromophenoxy)phenoxy]-ethyl]N-ethylthiocarbamate, m.p. 74°–76° C.;

from 2-[p-(m-tolyloxy)phenoxy]-ethanol and ethyl isothiocyanate there is obtained [2-[p-(m-tolyloxy)-phenoxy]-ethyl]N-ethylthiocarbamate, m.p. 72°–73° C.;

from 2-[p-(m-chlorophenoxy)phenoxy]-ethanol and ethyl isothiocyanate there is obtained [2-[p-(m-chlorophenoxy)phenoxy]-ethyl]N-ethylthiocarbamate, m.p. 81°–83° C.; and from 2-[p-(m-fluorophenoxy)phenoxy]-ethanol and ethyl isothiocyanate there is obtained [2-[p-(m-fluorophenoxy)phenoxy]-ethyl]N-ethylthiocarbamate, m.p. 102°–103° C.

EXAMPLE 3

A solution of 2.5 g of 2-[p-(p-fluorophenoxy)phenoxy]-ethanol in 25 ml of dimethylformamide is added dropwise during 20 minutes while stirring to a suspension of 0.5 g of sodium hydride (55% in oil) in 5 ml of dimethylformamide. The mixture is then allowed to stir at 40° C. for 4 hours, then treated dropwise with 1.18 g of dimethylcarbamoyl chloride and allowed to react at 40° C. for 16 hours. The cooled mixture is poured into 75 ml of ice/water and extracted three times with 50 ml of ethyl acetate each time. The extracts are washed three times with 50 ml of water each time, dried and evaporated. The residue is purified by chromatography on silica gel with n-hexane/ethyl acetate (85:15) to yield pure [2-[p-(p-fluorophenoxy)phenoxy]-ethyl]N,N-dimethylcarbamate; $n_D^{20}=1.5444$.

In an analogous manner:

from 2-[p-(m-fluorophenoxy)phenoxy]-ethanol and dimethylcarbamoyl chloride there is obtained [2-[p-(m-fluorophenoxy)phenoxy]-ethyl]N,N-dimethylcarbamate, $n_D^{20}=1.5442$.

II. PREPARATION OF THE STARTING MATERIALS

Example 4

6.8 g of ethylene carbonate and 2.3 g of tetrabutylammonium bromide are added to a solution of 13.8 g of p-(p-fluorophenoxy)phenol in 35 ml of dimethylformamide. After 4 hours at reflux there are added an additional 1.2 g of ethylene carbonate, and the mixture is heated at reflux for an additional 2 hours. The cooled mixture is poured into 150 ml of ice/water and extracted three times with 100 ml of ethyl acetate each time. The extracts are washed twice with 100 ml of saturated sodium chloride solution each time, dried and evaporated. The residue is purified by recrystallization from n-hexane/ethyl acetate to yield pure 2-[p-(p-fluorophenoxy)-phenoxy]-ethanol, m.p. 74°–76° C.

In an analogous manner:

from p-(α,α,α-trifluoro-m-tolyloxy)phenol and ethylene carbonate there is obtained 2-[p-(α,α,α-trifluoro-m-tolyloxy)phenoxy]-ethanol, $n_D^{20}=1.5315$;

from p-(m-bromophenoxy)phenol and ethylene carbonate there is obtained 2-[p-(m-bromophenoxy)-phenoxy]-ethanol, $n_D^{20}=1.611$;

from p-(m-fluorophenoxy)phenol and ethylene carbonate there is obtained 2-[p-(m-fluorophenoxy)-phenoxy]-ethanol, $n_D^{20}=1.5677$;

from 4-hydroxy-benzophenone and ethylene carbonate there is obtained 2-(p-benzoylphenoxy)-ethanol, m.p. 78°–80° C.;

from 4-benzylphenol and ethylene carbonate there is obtained 2-(p-benzylphenoxy)-ethanol, m.p. 50°–53° C.;

from p-(m-chlorophenoxy)phenol and ethylene carbonate there is obtained 2-[p-(m-chlorophenoxy)-phenoxy]-ethanol, $n_D^{20}=1.5897$;

from p-(3,5-dichlorophenoxy)phenol and ethylene carbonate there is obtained 2-[p-(3,5-dichlorophenoxy)-phenoxy]-ethanol, m.p. 56°–58° C.;

from p-(m-tolyloxy)phenol and ethylene carbonate there is obtained 2-[p-(m-tolyloxy)phenoxy]-ethanol, $n_D^{20}=1.5753$;

from p-(3-chloro-5-fluorophenoxy)phenol and ethylene carbonate there is obtained 2-[p-(3-chloro-5-fluorophenoxy)phenoxy]-ethanol, $n_D^{20}=1.5811$;

from p-(m-chloro-p-fluorophenoxy)phenol and ethylene carbonate there is obtained 2-[p-(m-chloro-p-fluorophenoxy)phenoxy]-ethanol, $n_D^{20}=1,5698$;

from o-fluoro-p-phenoxy-phenol and ethylene carbonate there is obtained 2-[o-fluoro-p-phenoxy-phenoxy]-ethanol, m.p. 36°–37° C.;

from m-fluoro-p-phenoxy-phenol and ethylene carbonate there is obtained 2-[m-fluoro-p-phenoxy-phenoxy]-ethanol, $n_D^{20}=1.5693$;

from p-(p-chlorophenylmercapto)phenol and ethylene carbonate there is obtained 2-[p-(p-chlorophenylmercapto)phenoxy]-ethanol, m.p. 68°–70° C.; and from p-phenylmercapto-phenol and ethylene carbonate there is obtained 2-(p-phenylmercapto-phenoxy)-ethanol, $n_D^{21}=1.6330$.

EXAMPLE 5

3.1 g of p-phenoxy-m-cresol and 0.74 g of ethylene oxide are heated to 150° C. for 2 hours in an autoclave in the presence of 1 drop of 50% sodium hydroxide. The cooled mixture is treated with ice/water and extracted twice with ethyl acetate. The extracts are washed with semi-saturated and saturated sodium chloride solution, dried over anhydrous sodium sulfate and evaporated. The residue is purified by chromatography on silica gel with n-hexane/ethyl acetate (2:1) to yield pure 2-(p-phenoxy-m-tolyloxy)-ethanol; $n_D^{20}=1.5788$.

In an analogous manner:

from p-(3,5-xylyloxy)-phenol and ethylene oxide there is obtained 2-[p-(3,5-xylyloxy)phenoxy]-ethanol, $n_D^{20}=1.5756$.

Example 6

A mixture of 6.13 g of p-(m-fluorophenoxy)phenol, 2.79 g of propylene oxide and 0.12 g of triethylamine is stirred at 90° C. for 18 hours. The cooled mixture is subsequently diluted with 100 ml of diethyl ether and washed successively twice with 50 ml of 2N hydrochloric acid each time, three times with 50 ml of 2N sodium hydroxide each time, with 50 ml of water and with 50 ml of saturated sodium chloride solution. After drying over anhydrous sodium sulfate and evaporation there is obtained 1-[p-(m-fluorophenoxy)phenoxy]-2-propanol of melting point 37°–39° C.

Example 7

A mixture of 5 g of p-(p-fluorophenoxy)phenol, 5.1 g of ethyl 2-bromopropionate and 4 g of potassium carbonate is stirred at reflux temperature in 25 ml of acetone for 24 hours. After evaporation of the solvent the residue is taken up in 100 ml of diethyl ether and 100 ml of water. The ether phase is washed with semi-saturated and saturated sodium chloride solution, dried over anhydrous sodium sulfate and evaporated. The residue is purified by chromatography on silica gel with n-hexane/ethyl acetate (19:1) to yield pure ethyl 2-[p-(p-fluorophenoxy)phenoxy]-propionate; $n_D^{20}=1.5304$.

1 g of lithium aluminium hydride is added to 20 ml of absolute diethyl ether and the solution in cooled by means of an ice-bath. While stirring, a solution of 5.8 g of ethyl 2-[p-(p-fluorophenoxy)phenoxy]-propionate in 50 ml of diethyl ether is added dropwise at such a rate that the temperature does not rise above 20° C. The mixture is subsequently allowed to stir at room temperature for 1.5 hours and then cautiously poured into 100 ml of ice-cold ammonium chloride solution. The mixture is extracted twice with diethyl ether, and the extracts are washed with semi-saturated and saturated sodium chloride solution, dried over anhydrous sodium sulfate and evaporated. The yellow oily residue is distilled in a bulb-tube at 140°–142° C./0.04 Torr to yield pure 2-[p-(p-fluorophenoxy)phenoxy]-propanol.

Example 8

32.3 g of hydroquinone are dissolved in 250 ml of dimethyl sulfoxide. While stirring and constantly introducing nitrogen there are successively added 100 ml of toluene and 30 g of 86% potassium hydroxide. Then the bath temperature is adjusted to 160° C. and the water is removed completely by means of a water separator. Thereafter the bath temperature is increased further and the toluene is distilled off until the internal temperature has reached 155° C. Then 40 g of 3-bromofluorobenzene are allowed to flow in and the mixture is held for 20 hours at this temperature. Thereafter the dimethyl sulfoxide is distilled off in a water-jet vacuum. The cooled residue is poured into ice/water, neutralized with hydrochloric acid and extracted three times with ethyl acetate. The extracts are washed twice with water and once with saturated sodium chloride solution, dried over anhydrous sodium sulfate and evaporated. The residue is purified by chromatography on silica gel with n-hexane/ethyl acetate (9:1) to yield p-(m-bromophenoxy)phenol; $n_D^{20}=1.6018$.

In an analogous manner:

from hydroquinone and 3-chlorobenzotrifluoride with the addition of a catalytic amount of copper powder there is obtained p-(α,α,α-trifluoro-m-tolyloxy)-phenol which distils in a bulb-tube at 140° C./0.05 Torr; $n_D^{20}=1.5370$.

Example 9

21.8 g of sodium hydride (55% in oil) are introduced into 100 ml of absolute pyridine and treated dropwise during 1 hour with 54.1 g of m-cresol in 200 ml of pyridine. After completion of the reaction 1.2 g of copper (I) chloride are added and subsequently 93.5 g of 4-bromoanisole are added dropwise at reflux temperature during 1 hour. After heating at reflux for 4 hours the pyridine is distilled off, whereby at the end the mixture is warmed to 170° C. (internal temperature). After 2 hours 350 ml of water are added dropwise while cooling with ice, followed by 500 ml of diethyl ether and an additional 150 ml of water. The mixture is suction filtered over Celite and the phases are separated. The organic phase is washed in sequence with 200 ml of 2N hydrochloric acid, three times with 100 ml of 2N sodium hydroxide each time, with 200 ml of water and with 200 ml of saturated sodium chloride solution. After drying over anhydrous sodium sulfate and evaporation there is obtained a brown-red oil which is firstly filtered over a five-fold amount of silica gel with n-hexane/diethyl ether and then distilled to yield pure p-(m-tolyloxy)anisole; b.p. 106°–108° C./0.04 Torr; $n_D^{20}=1.5738$.

77 g of p-(m-tolyloxy)anisole are dissolved in 360 ml of acetic acid and treated with 300 ml of 48% hydrobromic acid. Then the mixture is allowed to react at reflux temperature for 5 hours. The cooled solution is poured into 1.5 l of ice/water and extracted three times with 150 ml of methylene chloride each time. The organic solution is washed three times with 150 ml of water each time and with 150 ml of saturated sodium bicarbonate solution, dried over anhyrous sodium sulfate and evaporated. Distillation of the crude product yields pure p-(m-tolyloxy)phenol; b.p. 88°–89° C./0.04 Torr.

In an analogous manner:

from m-fluorophenol and 4-bromoanisole there is obtained p-(m-fluorophenoxy)anisole of boiling point 130°–131° C./0.2 Torr and therefrom with hydrobromic acid/acetic acid there is obtained p-(m-fluorophenoxy)-phenol, m.p. 53°–55° C.; and from 2-hydroxy-5-methoxy-toluene and bromobenzene there is obtained 5-methoxy-2-phenoxy-toluene of boiling point 102°–104° C./0.035 Torr and melting point 39°–42° C. and therefrom by methyl ether cleavage there is obtained p-phenoxy-m-cresol, m.p. 96°–99° C.

Likewise by methyl ether cleavage, from p-(m-chloro-p-fluorophenoxy)anisole there is obtained p-(m-chloro-p-fluorophenoxy)phenol, $n_D^{20}=1,4485$.

Example 10

6.1 g of phenol are dissolved in 40 ml of toluene and treated with a solution of 3.3 g of potassium hydroxide in 3 ml of water. Then the mixture is left to react on a water separator overnight. The toluene is subsequently distilled off. The solid residue is treated with 10.2 g of o-fluoro-p-bromoanisole and 0.1 g of copper (I) chloride and stirred at 180° C. (bath temperature) for 2 hours. The cooled mixture is treated with 100 ml of diethyl ether and 100 ml of water. The ether phase is washed twice with 50 ml of 2N sodium hydroxide, washed neutral with semi-saturated and saturated sodium chloride solution, dried over anhydrous sodium sulfate and evaporated. The residue is distilled in a bulb-tube at 104°–106° C./0.05 Torr to yield o-fluoro-p-phenoxy-anisole; $n_D^{20} = 1.5650$.

Therefrom there is obtained by methyl ether cleavage o-fluoro-p-phenoxy-phenol; $n_D^{20} = 1.5792$.

In an analogous manner:

from p-methoxyphenol and 1,3,5-bromochlorofluorobenzene there is obtained p-(3-chloro-5-fluorophenoxy)anisole ($n_D^{20} = 1.5752$) and therefrom by methyl ether cleavage there is obtained p-(3-chloro-5-fluorophenoxy)phenol; $n_D^{20} = 1.5821$.

III. FORMULATION EXAMPLES

Example 11

This example illustrates the preparation of an emulsifiable concentrate, using the compounds of formula I by admixture of the following ingredients, and of a ready-for-use spray liquor.

| Ingredient | g/l |
| --- | --- |
| Active ingredient of formula I | 250 |
| N—Methyl-2-pyrrolidone | 300 |
| Alkylphenol-ethylene oxide adduct | 35 |
| Calcium dodecylbenzenesulfonate | 15 |
| Cycloalkylepoxystearate | 25 |
| Aromatic solvent (mixture of $C_{10}$—alkylbenzenes) | ad 1000 ml |

The active ingredient is dissolved in the N-methyl-2-pyrrolidone, thereafter the remaining additives are added and dissolved, and the mixture is made up to mark with the aromatic solvent. This resulting emulsifiable concentrate is added to water to prepare a ready-for-use spray liquor, an emulsion (oil/water) which is stable for hours.

Example 12

This example illustrates the preparation of a spray powder, using the compounds of formula I by admixture of the following ingredients, and of ready-for-use spray liquors.

| Ingredient | Wt. % |
| --- | --- |
| Active ingredient of formula I | 25 |
| Silicic acid, hydrated (about 87% $SiO_2$) | 30 |
| Sodium lauryl sulfonate | 2 |
| Sodium lignosulfonate | 4 |
| Kaolin, mainly $Al_2[Si_2O_5](OH)_4$ | 39 |
|  | 100 |

The active ingredient is homogeneously mixed with the remaining formulation components in a suitable apparatus. The resulting powder is then finally ground in a suitable grinding apparatus, for example, pinned disc, hammer, ball or air-jet mill, to a particle size necessary for an optimum biological activity and then remixed. The resulting spray powder is spontaneously wetted by water and gives well-suspendible, ready-for-use spray liquors.

Example 13

This example illustrates the preparation of granulates using the compounds of formula I.

| Ingredient | Wt. % |
| --- | --- |
| Active ingredient of formula I | 5 |
| Tetrasodium salt of ethylenediamino-tetraacetic acid ($Na_4$—EDTA) | 1 |
| Pumice stone granulate 0.6–1.0 mm | 94 |
|  | 100 |

The pumice stone granulate is placed in a suitable mixing device and an aqueous solution of the $Na_4$-EDTA is sprayed on while stirring constantly. The mixture is dried at 110° C. and thereafter the active ingredient dissolved in a suitable solvent, for example, methylene chloride, is sprayed on the dry mixture. The solvent is evaporated by warming. There results a well-shakable granulate which can be applied to the soil or to the water by hand, with suitable granulate spreaders or even from aircraft. The porous structure of the pumice stone brings about in many cases a desired delayed release of the active ingredient over a long period.

Example 14

This example illustrates the preparation of a bait granulate using the compounds of formula I.

| Ingredient | Wt. % |
| --- | --- |
| Active ingredient of formula I | 2 |
| Soya bean oil | 30 |
| Maize cob granulate 0.5–2.5 mm | 68 |
|  | 100 |

The active ingredient is dissolved in the soya bean oil and this solution is homogeneously mixed with the ground maize in a suitable mixing apparatus. There results a well shakable granulate which can be applied to the soiL by hand or with a suitable granulate spreader. It is especially suitable for the control of fire ants.

I claim:

1. A compound of the formula

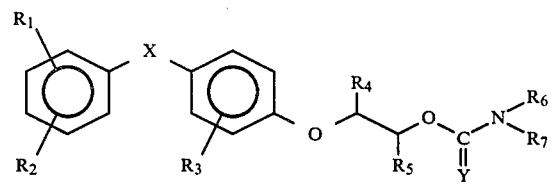

I wherein $R_1$ is hydrogen, halogen, or methyl, $R_2$ is halogen, methyl, or trifluoromethyl, $R_3$ is hydrogen, halogen, or methyl, $R_4$ is hydrogen and $R_5$ is hydrogen or methyl, $R_6$ is hydrogen, methyl, or ethyl, $R_7$ is methyl, ethyl, or isopropyl, X is oxygen, sulfur, methylene, or carbonyl, and Y is oxygen or sulfur, whereby, when X is sulfur, methylene, or carbonyl, or $R_3$ is halogen or methyl, $R_2$ can also be hydrogen.

2. The compound according to claim 1, wherein $R_2$ is halogen, methyl, or trifluoromethyl, and when X is sulfur, methylene, or carbonyl, $R_2$ can also be hydrogen.

3. The compound according to claim 2, wherein $R_1$ is hydrogen, m-halogen, or m-methyl.

4. The compound according to claim 2 or claim 3, wherein $R_2$ is p-fluoro, m-chloro, m-bromo, m-methyl, or m-trifluoromethyl.

5. The compound according to claim 1, wherein $R_2$ is hydrogen.

6. [2-[p-(m-Fluorophenoxy)phenoxy]-ethyl] N-ethylcarbamate.

7. [2-[p-(p-Fluorophenoxy)phenoxy]-ethyl] N-ethylcarbamate.

8. [2-(o-Fluoro-p-phenoxy-phenoxy)-ethyl] N-ethylcarbamate.

9. [2-[p-(m-Chlorophenoxy)phenoxy]-ethyl] N-ethylcarbamate.

10. A compound selected from the group consisting of

[2-[p-(p-Fluorophenoxy)phenoxy]-ethyl] N-isopropylcarbamate,

[2-[p-(p-fluorophenoxy)phenoxy]-ethyl] N-methylcarbamate,

[2-[p-($\alpha,\alpha,\alpha$-trifluoro-m-tolyloxy)phenoxy]-ethyl] N-ethylcarbamate,

[2-[p-(m-fluorophenoxy)phenoxy]-1-methyl-ethyl] N-methylcarbamate,

[2-[p-(m-fluorophenoxy)phenoxy]-1-methyl-ethyl] N-ethylcarbamate,

[2-(p-benzoylphenoxy)-ethyl] N-ethylcarbamate,

[2-(p-benzylphenoxy)-ethyl] N-ethylcarbamate,

[2-[p-(3,5-dichlorophenoxy)phenoxy]-ethyl] N-ethylcarbamate,

[2-[p-(m-tolyloxy)phenoxy]-ethyl] N-ethylcarbamate,

[2-[p-(3-chloro-5-fluorophenoxy)phenoxy]-ethyl] N-ethylcarbamate,

[2-[p-(m-chloro-p-fluorophenoxy)phenoxy]-ethyl] N-ethylcarbamate,

[2-(m-fluoro-p-phenoxy-phenoxy)-ethyl] N-ethylcarbamate,

[2-[p-(p-fluorophenoxy)phenoxy]-ethyl] N-ethylthiocarbamate,

[2-[p-(m-bromophenoxy)phenoxy]-ethyl] N-ethylthiocarbamate,

[2-[p-(m-tolyloxy)phenoxy]-ethyl] N-ethylthiocarbamate,

[2-[p-(m-chlorophenoxy)phenoxy]-ethyl] N-ethylthiocarbamate,

[2-[p-(m-fluorophenoxy)phenoxy]-ethyl] N-ethylthiocarbamate and

[2-[p-(p-fluorophenoxy)phenoxy]-ethyl] N,N-dimethylcarbamte.

11. A compound selected from the group consisting of

[2-(p-Phenylmercapto-phenoxy)-ethyl] N-ethylcarbamate,

[2-[p-(p-chlorophenylmercapto)phenoxy]-ethyl] N-ethylcarbamate,

[2-(p-phenoxy-m-tolyloxy)-ethyl] N-ethylcarbamate and

[2-[p-(3,5-xylyloxy)pheonoxy]-ethyl] N-ethylcarbamate.

12. A pesticidal composition which comprises an inert carrier material and, as the active ingredient, an amount which is effective as a pesticide of a compound of the formula:

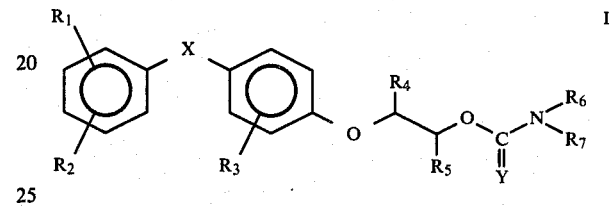

wherein $R_1$ is hydrogen, halogen, or methyl, $R_2$ is halogen, methyl, or trifluoromethyl, $R_3$ is hydrogen, halogen, or methyl, $R_4$ is hydrogen and $R_5$ is hydrogen or methyl, $R_6$ is hydrogen, methyl, or ethyl, $R_7$ is methyl, ethyl, or isopropyl, X is oxygen, sulfur, methylene, or carbonyl, and Y is oxygen or sulfur, whereby, when X is sulfur, methylene, or carbonyl, or $R_3$ is halogen or methyl, $R_2$ can also be hydrogen.

13. The pesticidal composition according to claim 12 wherein $R_2$ in formula I is halogen, methyl, or trifluoromethyl, and when X is sulfur, methylene, or carbonyl, $R_2$ can also be hydrogen.

14. The pesticidal composition according to claim 12 wherein the active ingredient is [2-[p-(m-fluorophenoxy)phenoxy]-ethyl] N-ethylcarbamate, [2-[p-(p-fluorophenoxy)phenoxy]-ethyl] N-ethylcarbamate, [2-(o-fluoro-p-phenoxy-phenoxy)-ethyl] N-ethylcarbamate or [2-[p-(m-chlorophenoxy)phenoxy]-ethyl] N-ethylcarbamate.

* * * * *